United States Patent
Hashizume et al.

(10) Patent No.: US 10,463,289 B2
(45) Date of Patent: Nov. 5, 2019

(54) LIQUID CONTROLLING METHOD

(75) Inventors: Nobuya Hashizume, Kyoto (JP);
Keishi Kitamura, Kyoto (JP);
Takahiro Nishimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 753 days.

(21) Appl. No.: 14/425,279

(22) PCT Filed: Sep. 3, 2012

(86) PCT No.: PCT/JP2012/005572
§ 371 (c)(1),
(2), (4) Date: Mar. 2, 2015

(87) PCT Pub. No.: WO2014/033796
PCT Pub. Date: Mar. 6, 2014

(65) Prior Publication Data
US 2015/0289793 A1 Oct. 15, 2015

(51) Int. Cl.
*A61B 5/15* (2006.01)
*A61B 5/155* (2006.01)
*G01T 7/02* (2006.01)
*A61B 5/153* (2006.01)
*A61B 5/157* (2006.01)

(52) U.S. Cl.
CPC ........ *A61B 5/150229* (2013.01); *A61B 5/153* (2013.01); *A61B 5/15003* (2013.01);
(Continued)

(58) Field of Classification Search
CPC .............. A61B 5/150229; A61B 5/153; A61B 5/150244; A61B 5/150236;
(Continued)

(56) References Cited

U.S. PATENT DOCUMENTS 5,380,665 A * 1/1995 Cusack .................. G01N 35/08
422/82
2001/0031932 A1 10/2001 Blake et al.
(Continued)

FOREIGN PATENT DOCUMENTS

EP 0607442 A1 7/1994
JP 05-99936 A 4/1993
(Continued)

OTHER PUBLICATIONS

International Search Report PCT/JP2012/005572 dated Oct. 9, 2012 with English translation.
(Continued)

*Primary Examiner* — Rene T Towa
(74) *Attorney, Agent, or Firm* — McDermott Will & Emery LLP

(57) ABSTRACT

Upon blood collection with a disclosed blood collecting apparatus, a part of a flow path adjacent to a suction drain mechanism is filled with a liquid different from the blood. A gas is inserted in the flow path between the liquid with which the part of the flow path adjacent to the suction drain mechanism is filled and a target blood to be collected. The suction drain mechanism pushes and pulls the gas by pushing and pulling the liquid during a standby time between collection and next collection, thereby controlling movement of the target blood. The suction drain mechanism pushes and pulls the liquid and the gas during the standby time, whereby the target blood is continuously moved. This allows prevention of coagulation of the target blood in the flow path.

4 Claims, 6 Drawing Sheets

(52) U.S. Cl.
CPC ........ *A61B 5/155* (2013.01); *A61B 5/150221* (2013.01); *A61B 5/150236* (2013.01); *A61B 5/150244* (2013.01); *A61B 5/150992* (2013.01); *G01T 7/02* (2013.01); *A61B 5/157* (2013.01)

(58) Field of Classification Search
CPC .......... A61B 5/150221; A61B 5/15003; A61B 5/150992; A61B 5/155; A61B 5/157; G01T 7/02
See application file for complete search history.

(56) References Cited

U.S. PATENT DOCUMENTS

2009/0111192 A1* 4/2009 Kitazawa ............ B01L 3/50273
436/172

2011/0060199 A1* 3/2011 Robinson ........... A61B 5/14532
600/316

2012/0000297 A1 1/2012 Hashizume et al.

FOREIGN PATENT DOCUMENTS

| JP | 2001-116666 A | 4/2001 |
|----|---------------|--------|
| JP | 2003-530188 A | 10/2003 |
| WO | 2010/106580 A1 | 9/2010 |

OTHER PUBLICATIONS

L. Convert et al., "A microvolumetric β blood counter for pharmacokinetic PET studies in small animals", IEEE Nuclear Sci., vol. 54, No. 1, 2007, pp. 1-8.

"Blood Sampler twilite", [online], Swisstrace, Internet URL: http://www.swisstrace.ch/blood-sampler-twilite.html Downloaded Aug. 14, 2012.

* cited by examiner

LIQUID CONTROLLING METHOD

CROSS REFERENCE TO RELATED APPLICATIONS

This application is a U.S. National Stage application under 35 U.S.C. § 371, of International Application PCT/JP2012/005572 filed on Sep. 3, 2012, which was published as WO 2014/033796 on Mar. 6, 2014. The application is incorporated herein by reference.

TECHNICAL FIELD

The present invention relates to a liquid controlling method used in a liquid collecting apparatus.

BACKGROUND ART

The following describes a liquid collecting apparatus taking a blood collecting apparatus that collects blood as one example. The blood collecting apparatus is used for quantitative analyses in nuclear medicine diagnosis (e.g., PET (Positron Emission Tomography)) and so on. In the nuclear medicine diagnosis, the quantitative analyses of information on a vital function, such as concentrations of nerve receptors and metabolism of tumor, require measurement of a time variation in agent concentration of plasma in arterial blood, i.e., a radioactive concentration. The following modes are adopted in an automatic blood collecting apparatus for measuring a radioactive concentration in blood. See, for example, Patent Literatures 1 and 2, and Non-Patent Literatures 1 and 2. The apparatus are used for measuring a radioactive concentration in arterial blood of small animals (e.g., mice, rats and so on). It should be noted that the automatic blood collecting apparatus in Patent Literature 1 differs from those in the other modes in purpose of use.

[Non-Patent Literature 1] In Non-Patent Literature 1, a radiation detector is installed to sandwich a part of a catheter inserted into arteria to measure a radioactive concentration in blood. An elongated diode has a length of 30 [mm] A tube containing blood is arranged along a long side of the diode, causing an increased detectable area. This achieves ensured detection efficiency of $\beta^+$-rays. The catheter includes one end connected to a syringe pump. The catheter pulls the syringe pump at a certain rate to draw blood. A flow rate of blood is calculated from the rate and a volume of blood is calculated from an internal diameter of the catheter, whereby a radioactive concentration is measured.

[Non-Patent Literature 2] As illustrated FIG. 7 in Non-Patent Literature 2, blood is returned into the vein V from the end of catheter C inserted into the arteria A. A LYSO detector D and a Perista pump P are installed in a part of the catheter C. $\beta^+$-rays in the arterial blood flowing inside the interior catheter C are annihilated to generate $\gamma$-rays. The $\gamma$-rays enter into the LYSO detector D to emit light, and the number of optical fibers F is counted with the light in a collecting box B. The Perista pump P controls a flow rate of blood. A control PC calculates a volume of blood from the flow rate and the internal diameter of the catheter, thereby measuring a radioactive concentration.

[Patent Literature 1] A flow path is switched by a five-way joint to repeat ejection of blood or a cleaning liquid and collection of blood.

[Patent Literature 2] The present application has suggested a technique concerning the automatic blood collecting apparatus. Patent Literature 2 discloses a process of pushing back blood into an animal using physiological saline solution containing heparin.

PATENT LITERATURE

Patent Literature 1: Japanese Patent Publication No. 2001-116666A

Patent Literature 2: International Publication WO2010-106580

NON-PATENT LITERATURE

Non-Patent Literature 1: L. Convert, G. M. Brassard, J. Cadorette, D. Rouleau, E. Croteau, M. Archambault, R. Fontaine, and R. Lecomte, "A microvolumetric β blood counter for pharmacokinetic PET studies in small animals, "IEEE Nuclear Sci, vol. 54, no. 1, 2007.

Non-Patent Literature 2: "Blood Sampler twilite", [online], Swisstrace, Internet URL: http://www.swisstrace.ch/blood-sampler-twilite.html

SUMMARY OF INVENTION

Technical Problem

However, the above modes each have the following drawbacks.

[Non-Patent Literature 1] Only the syringe pump is pulled, and thus no blood is pushed back into an animal. Accordingly, a long-time measurement causes a blood loss beyond a tolerance. As a result, long-time blood collection is impossible. In order to reduce a blood loss and thus burden to the animal, blood should be pushed back into animals.

[Non-Patent Literature 2] Since blood is returned back into a body of an animal through the vein, no blood loss occurs. On the other hand, an animal should be operated for inserting the catheter into not only the arteria but also into the vein. This leads to much expense in time and effort for operation. Moreover, a risk of failure in operation becomes high.

[Patent Literature 1] Blood is pushed back to an animal during a standby time between collection and next collection. However, the blood remains after being pushed back, which may cause blood coagulation there. Such a problem is not limited to blood. A liquid other than blood may coagulate upon collection.

[Patent Literature 2] Mixing starts from a contact interface of physiological saline solution containing heparin, causing blood dilution. Such a problem may arise.

The present invention has been made regarding the state of the art noted above, and its object is to provide a liquid controlling method that allows prevention of coagulation of a liquid to be collected.

Solution to Problem

To fulfill the above object, the present invention provides the following construction. One embodiment of the present invention discloses a liquid controlling method of controlling movement of a target liquid to be collected in a liquid collecting apparatus provided with a flow path having a given length and a suction drain device connected to the flow path for pushing and pulling a liquid. The method includes filling a part of the flow path adjacent to the suction drain device rather than a target liquid to be collected with a fluid composed of at least either a liquid or a gas, and pushing and pulling the fluid, with which the part of the flow path adjacent to the suction drain device is filled, during a standby time between collection and next collection using the suction drain device.

With the liquid controlling method according to the present embodiment, the suction drain device of the liquid collecting apparatus actively pushes and pulls the target liquid to be collected. This achieves liquid collection regardless of a supply source (collection source) of the liquid. For instance, when the target liquid to be collected is blood of an animal, blood collection is performable under decreased blood pressure depending on a physiological state of the animal. As a result, liquid collection is obtainable with decreased blood pressure of the animal. Moreover, the liquid collecting apparatus includes the flow path having a given length. Accordingly, the flow path with a given length set in advance and thus a known volume allow collection of a given volume of liquid without measuring a length and an amount of the target liquid to be collected using a volume measuring device (e.g., optical measuring device). In this manner, no need of the measuring device achieves reduction in size of the liquid collecting apparatus. Consequently, the liquid collecting apparatus can be installed close to a collecting source of the liquid (e.g., an animal). This achieves elimination of a factor responsible for a distortion of a concentration waveform, such as reduction, delay, or dispersion of a dead volume (indicating a void volume).

Upon the liquid collection using the liquid collecting apparatus mentioned above, a part of the flow path adjacent to the suction drain device rather than target liquid to be collected is filled with the fluid composed of a liquid or a gas. The suction drain device pushes and pulls the fluid with which the part of the flow path adjacent to the suction drain device is filled during a standby time between collection and next collection, whereby movement of the target liquid to be collected is controlled. The suction drain device pushes and pulls the fluid with which the flow path is filled during a standby time, whereby the target liquid to be collected is continuously moved. This allows prevention of coagulation of the target liquid to be collected in the flow path.

In the liquid controlling method of the present embodiment, the pushing and pulling the fluid, with which the part of the flow path adjacent to the suction drain device is filled, repeatedly causes control of reciprocating movement of the target liquid to be collected. Such is preferable. The reciprocating movement of the target liquid to be collected during the standby time allows more sufficient prevention of coagulation of the target liquid to be collected. Of course, the movement of the target liquid to be collected may be controlled by pushing and pulling the fluid composed of a liquid or a gas only in a period of the standby time during which coagulation may possibly occur.

Examples of the fluid include both a liquid and a gas, mentioned below, only a gas, and only a liquid. That is, for the fluid composed of a liquid and a gas as the first example, the part of the flow path adjacent to the suction drain device is filled with the liquid. Then the gas is inserted into the flow path between the liquid with which the part of the flow path adjacent to the suction drain device is filled and the target liquid to be collected. The suction drain device pushes and pulls the liquid with which the part of the flow path adjacent to the suction drain device is filled during the standby time, causing the gas to be pushed and pulled. Consequently, movement of the target liquid to be collected is controlled. Filling the flow path with the liquid and inserting the gas between the liquid and the target liquid to be collected allows reduction in volume of gas compressed or expanded due to push and pull by the suction drain device. This achieves movement of the target liquid to be collected with high accuracy. Consequently, the movement of the target liquid to be collected can be stopped immediately before a desired place using the flow path having a given length. As noted above, the suction drain device pushes and pulls the liquid and the gas during a standby time, whereby the target liquid to be collected is continuously moved. This allows prevention of coagulation of the target liquid to be collected in the flow path. Moreover, the gas is inserted between the liquid with which the part of the flow path adjacent to the suction drain device is filled and the target liquid to be collected. This allows prevention of mixing due to contact of the former liquid and the latter liquid (target to be collected). This also allows prevention of dilution of the target liquid to be collected resulting from the mixing.

For the fluid composed of a gas as the second example, the part of the flow path adjacent to the suction drain device rather than the target liquid to be collected is filled with the gas. The suction drain device pushes and pulls the gas with which the part of the flow path adjacent to the suction drain device is filled during a standby time, whereby movement of the target liquid to be collected is controlled. The flow path is filled with the gas, and the suction drain device pushes and pulls the gas during the standby time, whereby the target liquid to be collected is continuously moved. This allows coagulation of the target liquid to be collected in the flow path. In addition, the gas is only used for a medium without the other liquid. This allows mixing from contact of the target liquid to be collected and the other liquid. This also allows prevention of dilution of the target liquid to be collected resulting from the mixing.

For the fluid composed of a liquid as the last example, the part of the flow path adjacent to the suction drain device rather than the target liquid to be collected is filled with the liquid. The suction drain device pushes and pulls the liquid with which the part of the flow path adjacent to the suction drain device is filled during the standby time, whereby movement of the target liquid to be collected is controlled. The flow path is filled with the liquid and the suction drain device pushes and pulls the liquid during a standby time, whereby the target liquid to be collected is continuously moved. this allows coagulation of the target liquid to be collected in the flow path. The target liquid to be collected may be mixed with the liquid (to be used as a medium). However, the liquid with which an interface is generated from the target liquid to be collected is used as a liquid as the medium. Accordingly, this allows prevention of mixing of the target liquid to be collected with the liquid (to be used as a medium) due to contact to each other.

Moreover, for the fluid composed of a liquid and a gas or for the fluid composed of a liquid, the liquid with which the part of the flow path adjacent to the suction drain device is filled differs from the target liquid to be collected. The liquid with which the part of the flow path adjacent to the suction drain device is filled is moved in the flow path, whereby inside of the flow path is cleaned. Such is preferable. Inside the flow path is cleaned by the movement in the flow path of the liquid with which the part of the flow path adjacent to the suction drain device is filled. Accordingly, such an effect is produced that the target liquid to be collected remaining in the flow path is cleaned.

As mentioned above, blood has been described as one example of the target liquid to be collected in the liquid controlling method of the present embodiment. In this case, the liquid collecting apparatus performing the liquid controlling method corresponds to an apparatus that collects the blood (i.e., a blood collecting apparatus). It should be noted that the liquid is not limited to blood as long as it corresponds to the target liquid to be collected. For instance, physiological fluid other than blood (e.g., lymph, a protein-containing liquid, and so on), a fluorescence agent-containing liquid, and a mixed liquid used for an analyzer may be used.

Moreover, for the fluid composed of a liquid and a gas or for the fluid composed of a gas, the gas preferably has a volume in a range of 2 to 10 [μL]. Since the gas has a volume of 1 [μL] in a low control limit, twice the volume, i.e., 2 [μL] corresponds to the lowest value. The volume of gas becomes too small with less than the control limit. Accordingly, a possibility occurs that the liquid with which the part of the flow path adjacent to the suction drain device is filled contacts to the target liquid to be collected due to compression of the gas upon push and pull when the fluid is composed of the liquid and the gas, and when the gas is inserted into the flow path between the liquid and the target liquid to be collected. In contrast to this, the gas having a volume of more than 10 [μL] leads to impossible controlling. Accordingly, the movement of the target liquid to be collected is controlled with low accuracy.

Advantageous Effects of Invention

With the liquid controlling method of the present embodiment, the suction drain device pushes and pulls the fluid during a standby time, whereby the target liquid to be collected is continuously moved. This allows prevention of coagulation of the target liquid to be collected in the flow path.

EMBODIMENT 1

Figure 1:
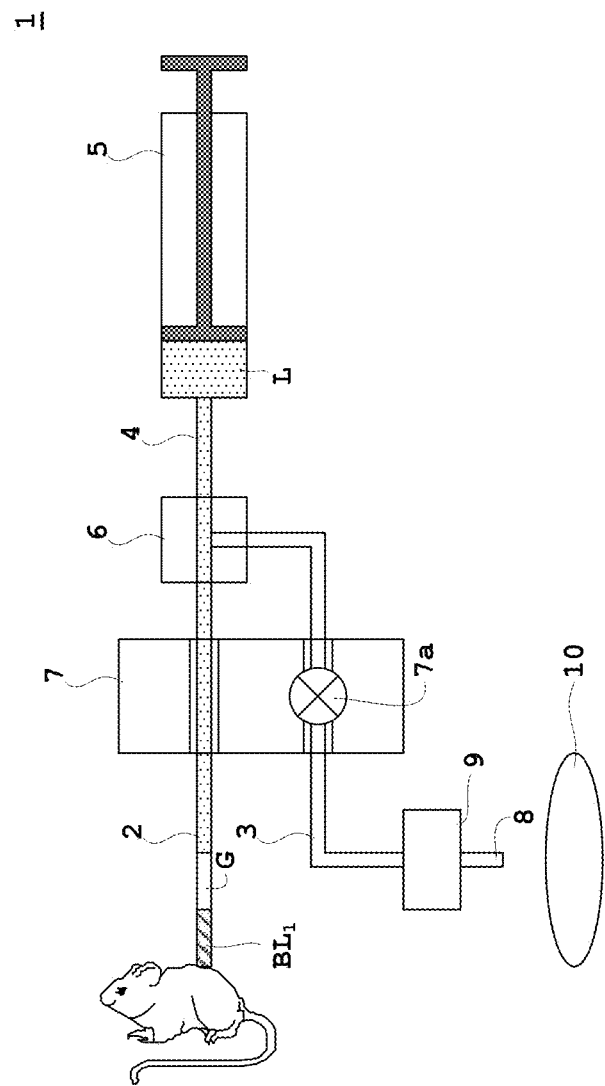
FIG. 1 schematically illustrates a blood collecting apparatus according to one embodiment of the present invention.

The following describes Embodiment 1 with reference to drawings. FIG. 1 schematically illustrates a blood collecting apparatus according to one embodiment of the present invention. Embodiment 1 as well as Embodiment 2 to be mentioned later describes blood as one example of a target liquid to be collected and a blood collecting apparatus as one example of a liquid collecting apparatus.

As illustrated in FIG. 1, a blood collecting apparatus 1 according to each embodiment of the present invention collects target blood to be collected as separated in a time series. Around the blood collecting apparatus 1, a container 10 is provided for storing collected blood. The Embodiment 1 as well as Embodiment 2 to be mentioned later measure a radioactive concentration in arterial blood of small animals (e.g., mice and rats). Moreover, a centrifuge (not shown) spins the container 10 for performing centrifugal separation. In each of the embodiments, the centrifugal separation is performed to blood. Accordingly a plasma separation is conducted and plasma as well as radiation each included in the plasma and blood cell resulting from the plasma separation is measured. The blood collecting apparatus 1 corresponds to the liquid collecting apparatus in the present invention.

The blood collecting apparatus 1 includes a flow path (a first flow path 2, a second flow path 3, and a third flow path 4 in the embodiments) having a given length, a suction drain mechanism 5 connected to the third flow path 4 of the flow path for pushing and pulling target blood to be collected, a connecting terminal 6 branching the flow path into a plurality of paths (two paths in each of the embodiments), a pinch valve 7 opening and closing the flow path (the first flow path 2 and the second flow path 3 in each of the embodiments), and a dropping port 8 connected to the branched flow path (the second flow path 3 in each of the embodiments) for dropping the separated target blood to be collected. The blood collecting apparatus 1 further includes a dropping port moving mechanism 9 moving the dropping port 8 for changing a position of dropping the separated target blood to be collected. The first flow path 2, the second flow path 3, and the third flow path 4 correspond to the flow path in the present invention. The suction drain mechanism 5 corresponds to the suction drain device in the present invention.

Except for the case of pressing back blood, a side adjacent to the collecting source (small animals in the present embodiment) corresponds to upstream, and a side adjacent to the dropping port 8 corresponds to downstream, taking a flow of blood upon collection as a reference. Accordingly, a flow path located upstream of the connecting terminal 6 is the first flow path 2, and a flow path located downstream of the connecting terminal 6 and upstream of the dropping port 8 is the second flow path 3. The suction drain mechanism 5 is so configured as to be connected to the third flow path 4 as another flow path different from the second flow path 3 connected to the dropping port 8.

A tube having a small section (i.e., a small diameter) is adopted for the flow path (the first flow path 2, the second flow path 3, and the third flow path 4) for reducing an amount of blood to be collected. In each of the present embodiments, two types of tubes are used. That is, a polyethylene tube having an internal diameter of 0.28 [mm] and a tube (SILASCON tube) having only a portion pinched by the pinch valve 7 made from SILASCON (Registered Trademark) as one type of silicone. The portion has an internal diameter of 0.5 [mm] and is softer than the polyethylene tube and thus has a restoring force. The first flow path 2 and the second flow path 3 of the flow path each have a predetermined length for achieving control of movement of a liquid (blood in each of the present embodiments) by merely push and pull with the suction drain mechanism 5. Of course, the third flow path 4 connected to the suction drain mechanism 5 may have a predetermined length.

A syringe pump is used as the suction drain mechanism 5. Usage of the syringe pump as the suction drain mechanism 5 achieves collection of the liquid (blood) by pushing and pulling the liquid (blood in each of the present embodiments) of several [μL] at a high rate and high accuracy. In addition, even if blood pressure varies depending on a physiological state of animals, stable blood collection is obtainable with no influence of the variation. As noted above, the suction drain mechanism 5 is a syringe pump that allows accurate push and pull of the liquid (blood). The first flow path 2 and second flow path 3 each having a predetermined length and a predetermined sectional area allows calculation of a volume. Consequently, blood flowing in the first flow path 2 or the second flow path 3 can be moved by a volume pushed and pulled by the suction drain mechanism 5.

Moreover, a liquid and a gas is used as the medium (fluid) to be pushed and pulled. Moreover, the gas to be pushed and pulled may be air. Alternatively, the gas may be an inert gas, representative of a noble gas such as helium, neon, and argon, or a nitrogen gas, that does not react with blood or a heparin solution. Moreover, the liquid to be pushed and pulled is not particularly limited. A cleaning liquid is preferably used as the liquid that is representative of a heparin solution used for cleaning a flow path or ejecting blood. In addition, a liquid with low viscosity, such as water or a mineral oil, is preferable for enhancing accuracy in control of the blood.

The numeral G in FIG. 1 as well as FIGS. 3 and 4 mentioned later denotes a gas. The numeral L in FIG. 1 as well as FIGS. 3 and 4 mentioned later denotes a liquid different from the target blood to be collected. The numeral $BL_1$ in FIGS. 1 and 3 as well as the numerals $BL_1$, $BL_2$, and $BL_3$ in FIG. 4 each denote the target blood to be collected. Moreover, in FIG. 1 as well as FIGS. 3 and 4 mentioned later, the liquid L is indicated by dotted hatching, and the gas G is indicated in white.

The connecting terminal 6 connects the first flow path 2, the second flow path 3, and the third flow path 4. In each of the present embodiments, the connecting terminal 6 uses a block made of a PDMS (polydimethylsiloxane) resin and having minute holes for the flow path. The holes are connected to the first flow path 2, the second flow path 3, and the third flow path 4 individually. Taking the upstream as a reference, the connecting terminal 6 branches the first flow path 2 into two paths, i.e., the second flow path 3 and the third flow path 4.

In each of the present embodiments, the pinch valve 7 is used as an opening and closing device for opening and closing the flow path. The pinch valve 7 is so configured as to close the flow path (the first flow path 2 and the second flow path 3) formed by the tube through application of pressure from outside the tube (see a "blocking part 7*a*" in FIG. 1 as well as FIGS. 3 and 4 mentioned later). The pinch valve 7 is also configured as to open the flow path (first flow path 2 and second flow path 3) formed by the tube through release of the pressure from outside the tube. Moreover, in each of the present embodiments, the pinch valve 7 is so configured as to close one of the two flow paths (the first flow path 2 and the second flow path 3) formed by the tube when opening the other of the flow paths. Consequently, the pinch valve 7 switches the blocking part 7*a* so as to close the second flow path 3 when opening the first flow path 2, and conversely so as to close the first flow path 2 when opening the second flow path 3.

The dropping port 8 dropping the collected blood is located above the container 10 storing the collected blood. The dropping port moving mechanism 9 changes a position of dropping the blood. In each of the present embodiments, the dropping port moving mechanism 9 adopts an electric slider with a stepping motor for changing a position of the dropping port 8 forward/backward and rightward/leftward (horizontally).

Moreover, the pinch valve 7 is so arranged as to have a distance to the collecting source (small animals in each of the present embodiments) in the flow in a range of 10 to 20 [cm]. Such is preferable. The pinch valve 7 arranged as to have the distance of 15 [cm] as the median of 10 to 20 [cm] is preferable for achieving both ready connection by the pinch valve 7 and prevention of liquid diffusion.

As illustrated in FIG. 1, the part of the flow path adjacent to the suction drain mechanism 5 rather than the target liquid to be collected (blood $BL_1$ to $BL_3$ in FIG. 1 as well as FIGS. 3 and 4) is filled with the fluid (the liquid L and/or the gas G). Then, the suction drain mechanism 5 pushes and pulls the fluid (the liquid L and/or the gas G) with which the part of the flow path adjacent to the suction drain mechanism 5 is filled during a standby time between collection and next collection, thereby controlling movement of the target liquid to be collected (blood $BL_1$ to $BL_3$).

Especially in Embodiment 1, the fluid is composed of both the liquid L and the gas G The part of the flow path adjacent to the suction drain mechanism 5 is filled with the liquid L. The gas G is inserted in the flow path between the target liquid to be collected (blood liquid $BL_1$ to $BL_3$) and the liquid L with which the part of the flow path adjacent to the suction drain mechanism 5 is filled. Then, the suction drain mechanism 5 pushes and pulls the liquid L with which the part of the flow path adjacent to the suction drain mechanism 5 is filled during a standby time, thereby pushing and pulling the gas G Consequently, the movement of the target liquid to be collected (blood $BL_1$ to $BL_3$) is controlled.

The gas G preferably has a volume in a range of 2 to 10 [μL]. As is mentioned later, the volume preferably falls within a range of 5 to 6 [μL], i.e., the median of 2 to 10 [μL] for achieving both prevention of contact of the liquid L to the target liquid to be collected (blood in each of the present embodiments) and maintained accuracy in control of the target liquid to be collected (blood), the part of the flow path adjacent to the suction drain device being filled with the liquid L.

Figure 2:
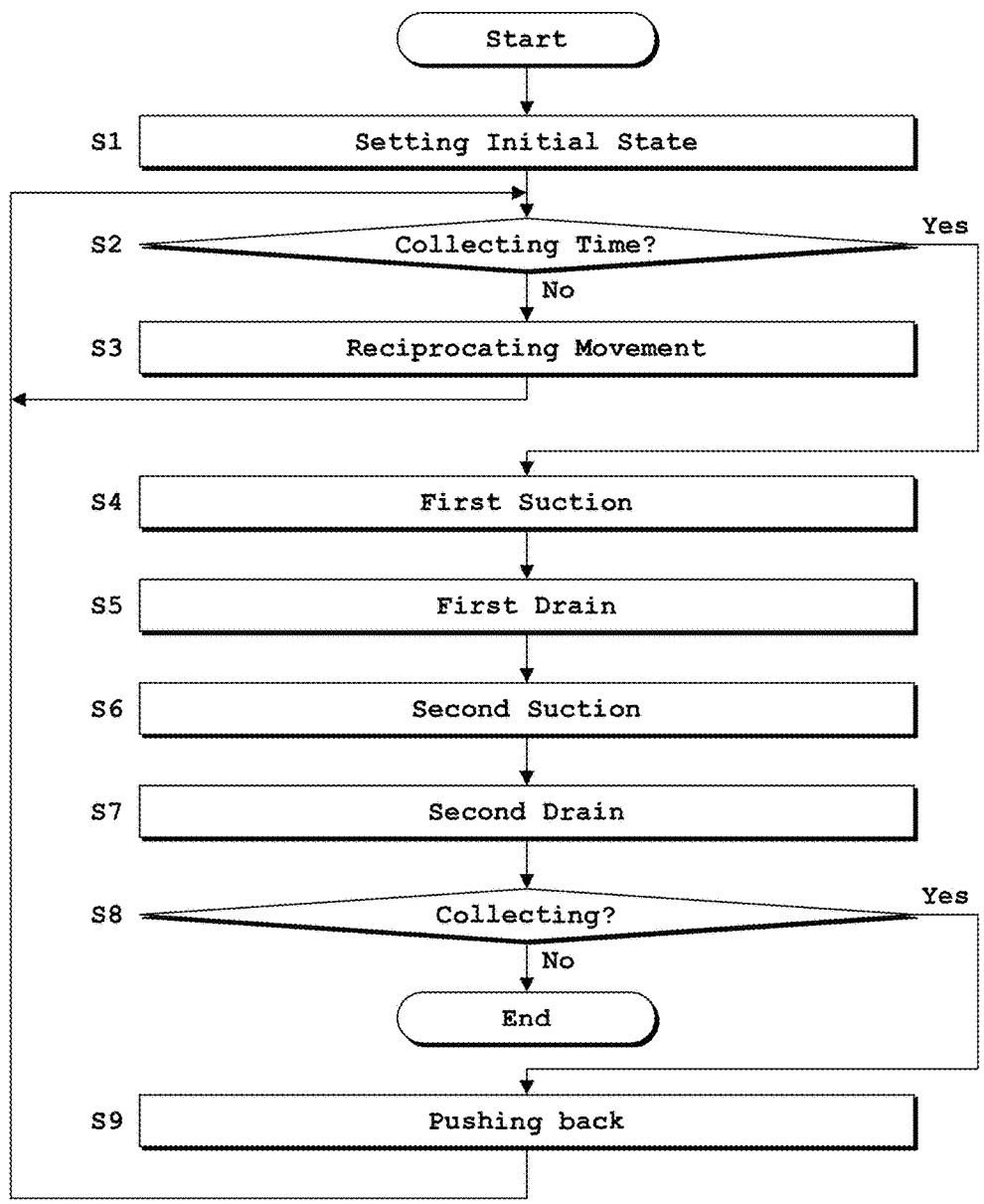
FIG. 2 is a flow chart of a series of blood collecting processes according to the embodiment.
Figure 3:
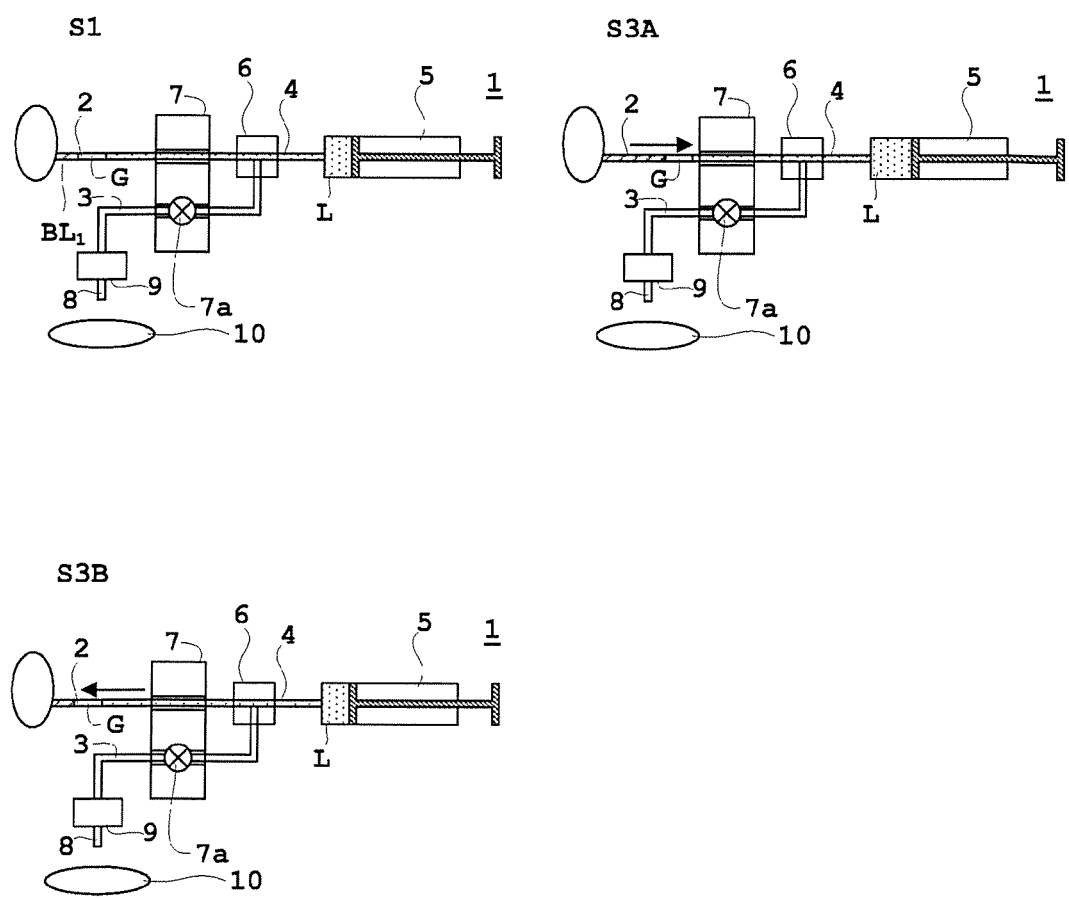
FIGS. 3 and 4 each schematically illustrate the series of blood collecting processes in turn according to the embodiment.
Figure 4:
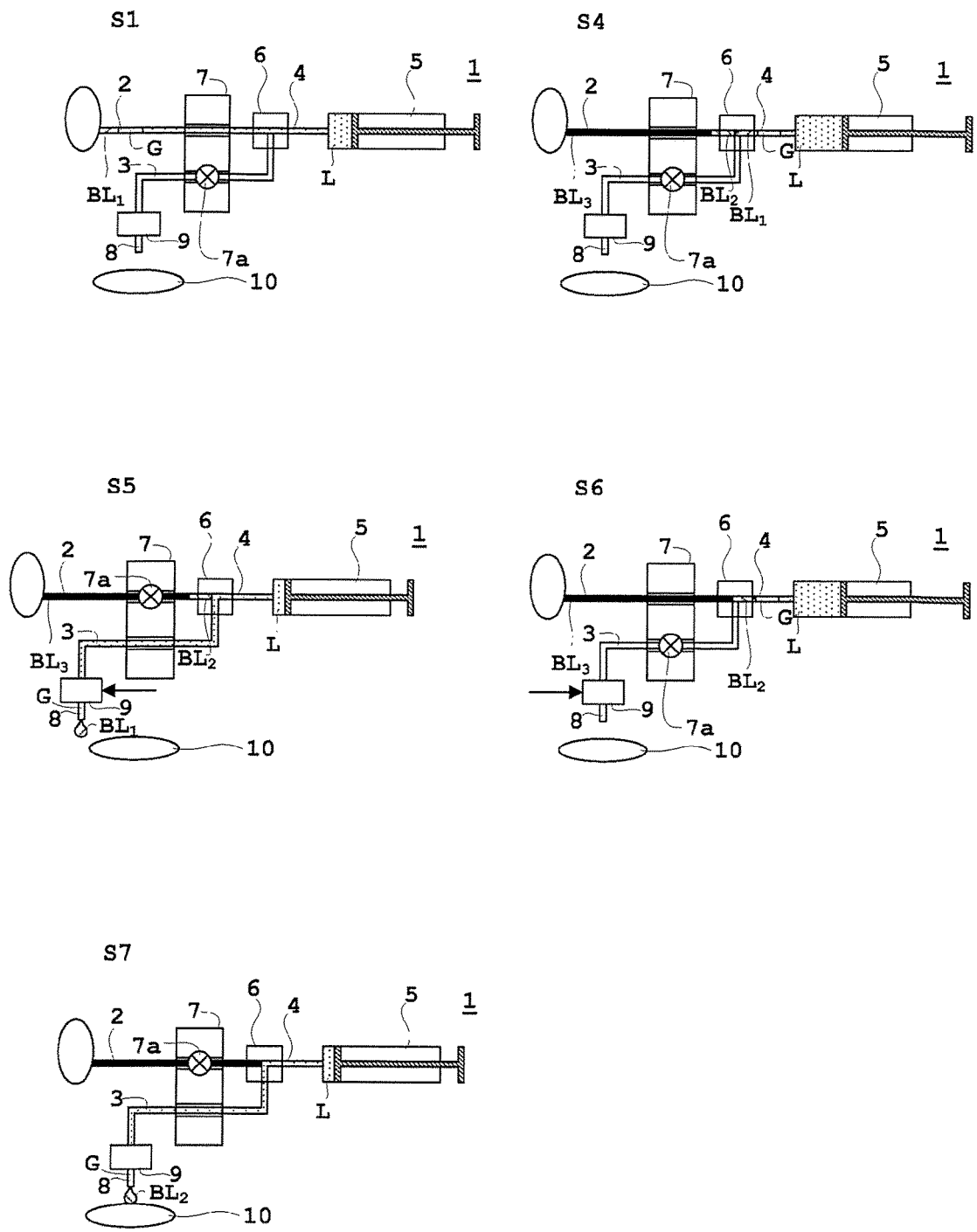

The following describes a series of blood collection processes with reference to FIGS. 2 to 4. FIG. 2 is a flow chart of a series of blood collecting processes according to each of the present embodiments. FIGS. 3 and 4 each schematically illustrate the series of blood collecting processes in turn according to Embodiment 1. Moreover, in FIGS. 3 and 4, a given amount of target blood to be collected (waste liquid) drained in an initial state (denoted by the numeral $BL_1$) is indicated by hatching with diagonal lines extending to the upper right. The finally collected blood (denoted by the numeral $BL_2$) is indicated by hatching with diagonal lines extending to the upper left. The other blood (denoted by the numeral $BL_3$) is indicated in black. In a step S1 of setting an initial state, the part of the flow path adjacent to the suction drain mechanism 5 is filled with the liquid L, and the part of the flow path adjacent to the collecting source (small animals in each of the present embodiments) as a liquid source is filled with the gas G.

(Step S1) Setting Initial State

FIG. 3 illustrates a step S1 in an initial state prior to blood collection. If blood is entirely pushed and pulled into the animal, a gas such as air is inserted into the animal to cause the animal to drop dead. In order to avoid this, a given amount of blood $BL_1$ is sucked, and accordingly a small amount of blood $BL_1$ remains outside the body of the animal. More specifically, the pinch valve 7 opens the first flow path 2 and closes the second flow path 3. Under this state, the suction drain mechanism 5 sucks a given amount of blood $BL_1$. This condition is set as an initial state. The suction by a given amount of blood $BL_1$ causes the gas G to be inserted in the flow path between the liquid L with which the part of the flow path adjacent to the suction drain mechanism 5 is filled and the sucked blood $BL_1$.

(Step S2) Collecting Time?

If the process does not reach a blood collection time, a step S3 of reciprocating movement is performed. If the process reaches the blood collection time, a step S4 of first suction is performed.

(Step S3) Reciprocating Movement

FIG. 3 illustrates a step S3A indicating suction of blood. The suction drain mechanism 5 sucks the liquid L with which the part of the flow path adjacent to the suction drain mechanism 5 is filled, thereby sucking the gas G and the blood. FIG. 3 illustrates a step S3B indicating push back of the blood. The suction drain mechanism 5 pushes back the liquid L with which the part of the flow path adjacent to the suction drain mechanism 5 is filled, thereby pushing back the gas G and the blood. With the steps S3A and S3B, the suction drain mechanism 5 pushes and pulls the liquid L with which the part of the flow path adjacent to the suction drain mechanism 5 is filled during a standby time between collection and next collection, thereby pushing and pulling the gas G Consequently, the movement of the target blood to be collected is controlled. The process returns to the step S2 and the steps S2 and S3 are repeatedly performed until the process reaches a next blood collection time. Accordingly, the liquid L is pushed and pulled repeatedly, the part of the flow path adjacent to the suction drain mechanism 5 being filled with the liquid L. Consequently, the gas G is pushed and pulled repeatedly, causing control of the reciprocating movement of the target blood to be collected.

During the above step, the first flow path 2 is kept open and the second flow path 3 is kept closed. Moreover, an amount of liquid to be pushed and pulled is not particularly limited. The amount is sufficient that allows prevention of coagulation. When the target liquid to be collected is blood, an amount of blood to be pushed and pulls falls in a range of 1 to 2 [μL]. Moreover, the blood is pushed back to the initial state in the step S1 or to a condition where a small amount of blood remains outside the body of the animal. As noted above, the suction drain mechanism 5 repeatedly pushes and pulls a minute amount of blood in a range of 1 to 2 [μL] to continuously move the blood, whereby blood coagulation is avoidable.

(Step S4) First Suction

When the blood collection starts and immediately the suction drain mechanism 5 is pulled to suck blood $BL_2$ and $BL_3$ from the animal. More specifically, the pinch valve 7 keeps the first flow path 2 opened and the second flow path 3 closed. Under this condition, following suction of the given amount of target blood to be collected $BL_1$ under the initial state, the suction drain mechanism 5 further sucks the blood $BL_2$ and $BL_3$ until the blood $BL_1$ is located at the connecting terminal 6. As is described in the step S3, suction of the liquid L and the gas G causes suction of blood.

(Step S5) First Drain

For collecting blood $BL_2$ in the body at a blood collection time, blood $BL_1$ outside the body (i.e., a given amount of target blood to be collected $BL_1$ pulled out in the initial state) is discarded, and blood $BL_2$ to flow next is collected. In order to achieve this, the blood $BL_1$ to be discarded is pulled out to a portion closer to the suction drain mechanism 5 than the connecting terminal 6 (see the right of FIG. 3). The blocking part 7a of the pinch valve 7 is switched from the second flow path 3 to the first flow path 2. Then, the suction drain mechanism 5 presses to eject the blood $BL_1$ from the dropping port 8 through the second flow path 3. More specifically, after the first suction in the step S2, the pinch valve 7 causes the first flow path 2 to be close and the second flow path 3 to be opened. Under such a condition, a given amount of target blood to be collected $BL_1$ pulled out in the initial state is pushed back to drain and eject the blood $BL_1$ from the dropping port 8 through the second flow path 3. At this time, the dropping port moving mechanism 9 causes the dropping port 8 to move externally from above the container 10, and then blood $BL_1$ is ejected. As is also described in the step S3, the liquid L and the gas G are pushed back, whereby the blood is pressed back.

The gas G is preferably stopped with the dropping port 8 upon ejecting the blood $BL_1$ by the first drain in the step S5. However, denoting the entire volume of gas G by V, there is no need to stop the entire volume V of gas G with the dropping port 8. Especially, the gas G as air is pushed out completely with droplets of blood to be ejected. Consequently, it is more preferable that half the entire volume V of gas G, i.e., 0.5V, is also pushed out of the dropping port 8. Accordingly, the gas G of 0.5V remains in the flow path. After dropping, the condition of the process returns to a step S6 to be mentioned later while the dropping port 8 sucks the redundant ejected gas G (air in this case) of 0.5V. Consequently, the volume returns to the entire volume V since the sucked gas G of 0.5V is added to obtain a volume of 0.5V+0.5V.

As a result, enhanced dripping with the dropping port 8 is obtainable with no blood $BL_1$ remaining. At this time, in the step S5 of FIG. 4, the gas G flows into the dropping port 8 connected to the second flow path 3, and thus the liquid L directly contacts the blood $BL_2$ at a bifurcation portion of the connecting terminal 6. However, the blocking part 7a of the pinch valve 7 is located in the first flow path 2 and thus closes the first flow path 2 while opening the second flow path 3. Under such a condition, the liquid L absolutely flows to the second flow path 3 without flowing into the first flow path 2. Consequently, mixing of the liquid L is avoidable. Especially, using a heparin solution for the liquid L causes an interface between the heparin solution and the blood. This achieves more sufficient prevention of mixing of the liquid L. Moreover, in each of the present embodiments, the tube with a smaller sectional area (i.e., a smaller diameter) is used. Accordingly, a contact section of the liquid L and the blood is small, leading to more sufficient prevention of the mixing of the liquid L.

Subsequently, the suction drain mechanism 5 sucks the liquid L and the gas G until the gas G reaches the bifurcation portion of the connecting terminal 6. Accordingly, the gas G is inserted between the liquid L and the blood $BL_2$ in the flow path.

(Step S6) Second Suction

The dropping port moving mechanism 9 moves the dropping port 8 above the container 10. The blocking part 7a of the pinch valve 7 is switched from the first flow path 2 to the second flow path 3. The suction drain mechanism 5 sucks the blood $BL_2$ to a portion closer to the suction drain mechanism 5 than the connecting terminal 6 (see the right of FIG. 3). Specifically, after the first ejection in the step S5, the pinch valve 7 opens the first flow path 2 and closes the second flow path 3. Under such a condition, the suction drain mechanism 5 sucks the blood $BL_2$ such that the target blood to be collected $BL_2$ reaches the portion closer to the suction drain mechanism 5 than the connecting terminal 6. At this time, the blood $BL_3$ is sucked following suction of the blood $BL_2$. As is also described in the steps S3 and S4, the liquid L and the gas G are sucked, whereby the blood is sucked.

(Step S7) Second Drain

The blocking part 7a of the pinch valve 7 is switched from the second flow path 3 to the first flow path 2. The suction drain mechanism 5 is pushed to drop the blood $BL_2$ from the dropping port 8 to the container 10. More specifically, after the second drain in the step S6, the pinch valve 7 closes the first flow path 2 and opens the second flow path 3. Under such a condition, the target blood to be collected $BL_2$ pulled out through the second drain in the step S6 is pushed back to drain and collect the target blood from the dropping port 8 via the second flow path 3. As is also described in the steps S3 and S5, the liquid L and the gas G are pushed back, whereby the blood is pushed back.

Similar to the step S5, it is also preferable upon collection of the blood $BL_2$ through the second drain in the step S7 to stop the gas G with the dropping port 8. Similar to the step S5, it is more preferable to half the entire volume V, i.e., 0.5V, is pushed out of the dropping port 8 for completely pushing out the blood to be collected in the form of ink droplets. After dropping, the condition of the process returns to a step S9 to be mentioned later while the dropping port 8 sucks the redundant pushed gas G (air in this case) of 0.5V. Consequently, the volume returns to the entire volume V since the sucked gas G of 0.5V is added to obtain a volume of 0.5V+0.5V.

As noted above, a required amount of blood $BL_2$ to be collected can be dropped with no blood $BL_2$ remaining in the dropping port 8. At this time, the liquid L directly contacts the blood $BL_3$ also in the step S7 of FIG. 4, which is similar in the step S5. However, the first flow path 2 is closed and the second flow path 3 is opened. Under such a condition, the liquid L absolutely flows into the second flow path 3 without flowing into the first flow path 2, allowing prevention of mixing of the liquid L.

Subsequently, the suction drain mechanism 5 sucks the liquid L and the gas G until the gas G reaches the bifurcation portion of the connecting terminal 6. Accordingly, the gas G is inserted between the liquid L and the blood $BL_3$ in the flow path.

(Step S8) Collecting?

Subsequently, if blood collection is performed, the process returns to the step S2 after the step S9 of pushing back, and the processes in step S2 to S8 are similarly repeated. If no blood collection is performed, a series of blood collection processes is completed.

(Step S9) Pushing back

After dropping, the blocking part 7a of the pinch valve 7 is switched from the first flow path 2 to the second flow path 3. Then the suction drain mechanism 5 is pressed to push back the blood $BL_3$ into the animal. Then the process returns to the step S2. More specifically, after the second drain in the step S7, the pinch valve 7 opens the first flow path 2 and closes the second flow path 3. Under such a condition, the suction drain mechanism 5 pushes back the target blood to be collected $BL_3$ into the animal as the collecting source to introduce the condition to the initial state. As noted above, after the pushing back in the step S9, determination of the collecting time in the step S2, the reciprocating movement in the step S3, the first suction in the step S4, the first drain in the step S5, the second suction in the step S6, and the second drain in the step S7 are repeatedly performed. As is also described in the steps S3, S5, and S7, the liquid L and the gas G are pushed back, whereby the blood is pushed back.

With the liquid controlling method of Embodiment 1, the suction drain mechanism 5 of the blood collecting apparatus 1 in Embodiment 1 actively pushes and pulls the target liquid to be collected (blood in the present embodiment), achieving collection of the liquid (blood) regardless of the condition of the supply source (collecting source) of the liquid (blood). As in each of the present embodiments, when the target liquid to be collected is blood of animals, blood collection is performable under decreased blood pressure due to a physiological state of animals. As a result, liquid (blood) collection is obtainable with decreased blood pressure of animals. Moreover, the liquid collecting apparatus 1 includes the flow path (the first flow path 2, the second flow path 3, and the third flow path 4 in each of the present embodiments) having a given length. Accordingly, the flow path with a given length set in advance and thus a known volume allows collection of a given amount volume of liquid without measuring a length and an amount of the target liquid to be collected using a volume measuring device (e.g., optical measuring device). In this manner, no need of the measuring device allows reduction in size of the liquid collecting apparatus (the blood collecting apparatus 1 in each of the present embodiments). Consequently, the liquid collecting apparatus can be installed adjacent to a collecting source (e g, animal) of the liquid.

Upon collection of the liquid (blood) using the blood collecting apparatus 1 having the above construction, the part of the flow path adjacent to the suction drain mechanism 5 rather than the target liquid to be collected (the blood $BL_1$ to $BL_3$ in FIGS. 1, 3 and 4) is filled with the fluid composed of at least either the liquid L or the gas G Then the suction drain mechanism 5 pushes and pulls the fluid (liquid L and gas G) with which the part of the flow path adjacent to the suction drain mechanism 5 is filled during a standby time between collection and next collection, whereby movement of the target liquid to be collected (blood) is controlled. The flow path is filled with the fluid (liquid L and gas G), and the suction drain mechanism 5 pushes and pulls the fluid (liquid L and gas G) during a standby time, whereby the target liquid to be collected (blood) is continuously moved. This allows prevention of coagulation of the target liquid to be collected (blood) in the flow path.

The present embodiment 1 adopts both the liquid L and the gas G as the fluid. That is, the fluid of the present embodiment 1 is composed of the liquid L and the gas G The part of the flow path adjacent to the suction drain mechanism 5 is filled with the liquid L. Then gas G is inserted in the flow path between the liquid L with which the part of the flow path adjacent to the suction drain mechanism 5 is filled and the target liquid to be collected (blood $BL_1$ to $BL_3$). The suction drain mechanism 5 pushes and pulls the liquid L with which the part of the flow path adjacent to the suction drain mechanism 5 is filled during a standby time to push and pull the gas G, whereby movement of the target liquid to be collected (blood) is controlled. Filling the flow path with the liquid L and inserting the gas G between the liquid and the target liquid to be collected (blood) allows reduction in volume of gas G compressed or expanded due to push and pull by the suction drain mechanism 5. This achieves movement of the target liquid to be collected (blood) with high accuracy. Consequently, the target liquid to be collected (blood) can be stopped immediately before a desired place (e.g., a position of the supply source of the blood returned with pushing back in the step S3) using the flow path having a given length. As noted above, the suction drain mechanism 5 pushes and pulls the liquid L and the gas G during a standby time, whereby the target liquid to be collected (blood) is continuously moved. This allows prevention of coagulation of the target liquid to be collected (blood) in the flow path. Moreover, gas is inserted between the liquid with which the part of the flow path adjacent to the suction drain mechanism 5 is filled and the target liquid to be collected (blood). This allows prevention of mixing due to contact of the former liquid L and the latter liquid (target to be collected) (blood). This also allows prevention of dilution of the target liquid to be collected (blood) resulting from the mixing.

In the present embodiment 1, the gas G is repeatedly pushed and pulled by repeatedly pushing and pulling the liquid L with which the part of the flow path adjacent to the suction drain mechanism 5 is filled, whereby reciprocating movement of the target liquid to be collected (blood) is controlled. Such is preferable. Reciprocating movement of the target liquid to be collected (blood) during the standby time allows more sufficient prevention of coagulation of the target liquid to be collected (blood).

Moreover, for the fluid composed of the liquid L and the gas G as in the present embodiment 1, the liquid with which the part of the flow path adjacent to the suction drain mechanism 5 differs from the target liquid to be collected (blood). Inside the flow path is cleaned by the movement in the flow path of the liquid L with which the part of the flow path adjacent to the suction drain mechanism 5 is filled. Such is preferable. As mentioned above in the present embodiment 1, a heparin solution, water, or a mineral oil is preferably used for the liquid L to clean inside the flow path. Inside the flow path is cleaned by the movement in the flow path of the liquid with which the part of the flow path adjacent to the suction drain mechanism 5 is filled. Accordingly, such an effect is produced that the target liquid to be collected (blood) remaining in the flow path is cleaned.

The liquid controlling method in each of the present embodiments is described taking the target liquid to be collected as one example of the blood. In this case, the liquid collecting apparatus performing the liquid controlling method corresponds to an apparatus for performing blood collection, i.e., a blood collecting apparatus 1.

Moreover, for the fluid composed of the liquid L and the gas G as in the present embodiment 1, the gas G preferably has a volume in a range of 2 to 10 [µL]. Since the gas has a volume of 1 [µL] in a low control limit, twice the volume, i.e., a value 2 [µL] corresponds to the lowest value. The volume of gas G becomes too small with less than the control limit. Accordingly, a possibility occurs that the liquid L with which the part of the flow path adjacent to the suction drain mechanism 5 contacts to the target liquid to be collected (blood) due to compression of the gas G upon push and pull when the fluid L is composed of the liquid L and the gas G and when the gas G is inserted into the flow path between the liquid L and the target liquid to be collected (blood). In contrast to this, the gas G having a volume of more than 10 [µL] leads to impossible controlling. Accordingly, the movement of the target liquid to be collected (blood) is controlled with low accuracy.

EMBODIMENT 2

The following describes Embodiment 2 with reference to drawings. Embodiment 1 mentioned above adopts both the liquid and gas as the fluid. In contrast to this, Embodiment 2 adopts either a liquid or a gas as the fluid. Accordingly, Embodiment 2 uses the liquid L and the gas G as in FIGS. 1, 3, and 4.

That is, in the present embodiment 2, the liquid L or the gas G is used as a medium (fluid) to be sucked and drained.

The gas G is not particularly limited. For instance, the gas may be air as in Embodiment 1. Alternatively, the gas may be an inert gas, representative of a noble gas such as helium, neon, and argon, or a nitrogen gas, that does not react with blood or a heparin solution. Moreover, the liquid L is not particularly limited. For instance, the liquid L may be a heparin solution as in Embodiment 1, water, or a mineral oil.

Since a flow chart of steps S1 to S9 is same as that of Embodiment 1, the description thereof is to be omitted.

For the fluid composed of the gas G, the part of the flow path adjacent to the suction drain mechanism 5 rather than the target liquid to be collected (blood) is filled with the gas L. The suction drain mechanism 5 pushes and pulls the gas G with which the part of the flow path adjacent to the suction drain mechanism 5 during a standby time, whereby movement of the target liquid to be collected (blood) is controlled. The flow path is filled with the gas G and the suction drain mechanism 5 pushes and pulls the gas G during a standby time, whereby the target liquid to be collected (blood) is continuously moved. This allows prevention of coagulation of the target liquid to be collected (blood) in the flow path. In addition, the gas G is only used for a medium without other liquid. This allows prevention of mixing due to contact of the target liquid to be collected (blood) and the other liquid. This also allows prevention of dilution of the target liquid to be collected (blood) resulting from the mixing.

For the fluid composed of the liquid L, the part of the flow path closer to the suction drain mechanism 5 than the target liquid to be collected (blood) is filled with the liquid L. The suction drain mechanism 5 pushes and pulls the liquid L with which the part of the flow path adjacent to the suction drain mechanism 5 during a standby time, whereby movement of the target liquid to be collected (blood) is controlled. The flow path is filled with the liquid L and the suction drain mechanism 5 pushes and pulls the liquid L during a standby time, whereby the target liquid to be collected (blood) is continuously moved. This allows prevention of coagulation of the target liquid to be collected (blood) in the flow path. The target liquid to be collected (blood) may possibly be mixed with the liquid L (to be used as a medium). However, the liquid L with which an interface is generated from the target liquid to be collected (blood) is used as the liquid L for the medium. Accordingly, this allows prevention of mixing of the target liquid to be collected (blood) with the liquid L (to be used as a medium) due to contact to each other.

The present invention is not limited to the above embodiments, but may be modified as under.

(1) In the liquid controlling method used in the liquid collecting apparatus (blood collecting apparatus 1 in each of the present embodiments) mentioned above, blood has been described as one example of the target liquid to be collected. However, the blood is not limitative for the target liquid to be collected. For instance, physiological fluid other than blood (e.g., lymph or protein-containing liquid), a fluorescence agent-containing liquid, or a mixed liquid for an analyzer is adoptable.

(2) The each of the present embodiments mentioned above describes the blood collecting apparatus 1 illustrated in FIG. 1. However, the construction as in FIG. 1 is not limitative. A liquid collecting apparatus provided with a flow path having a given length and a suction drain device (suction drain mechanism) connected to the flow path for pushing and pulling the liquid is applicable to a liquid collecting apparatus as illustrated in FIG. 5 or 6.

Figure 5:
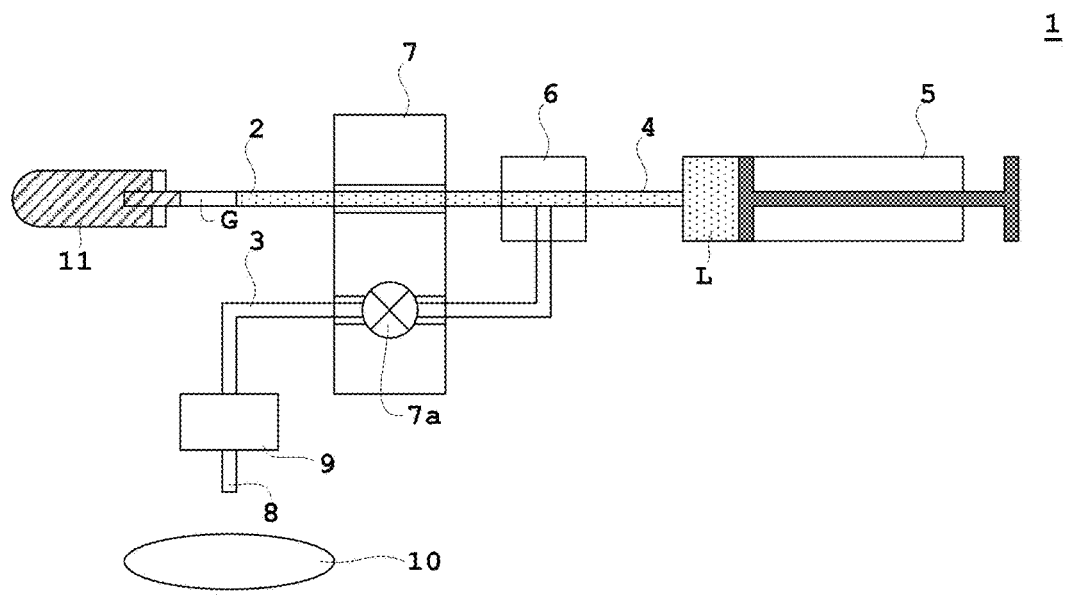
FIG. 5 schematically illustrates a liquid collecting apparatus according to one modification of the present invention.

(3) For instance, when blood is accommodated in the container 11 with an anticoagulant coated thereon for preventing blood coagulate as in FIG. 5 or when the liquid other than the blood as the target liquid to be collected is accommodated in the container 11 as in the modification (1), the target liquid to be collected (hatching with diagonal lines extending to the upper right) is sucked under the state where the first flow path 2 is inserted into the container 11, and the suction drain mechanism 5 pushing and pulling the liquid L with which the part of the flow path adjacent to the suction drain mechanism 5 is filled during the standby time, whereby the gas G is pressed and pulled. Consequently, movement of the target liquid to be collected is controlled. Such is adoptable. In this modification, only the liquid L or the gas G may be the medium (fluid) to be pushed and pulled.

Figure 6:
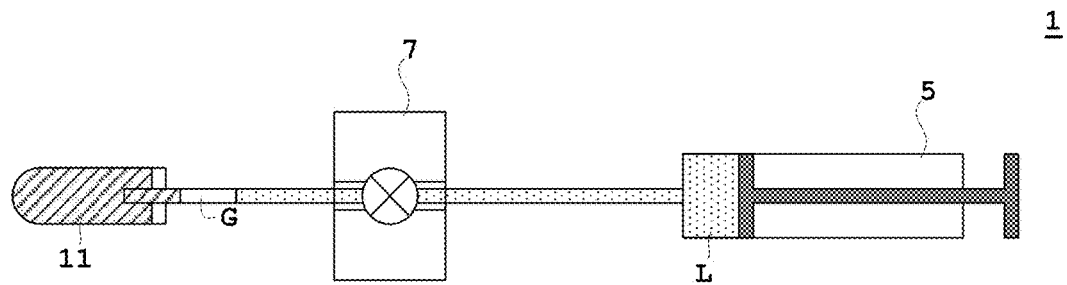
FIG. 6 schematically illustrates a liquid collecting apparatus according to another modification of the present invention.
Figure 7:
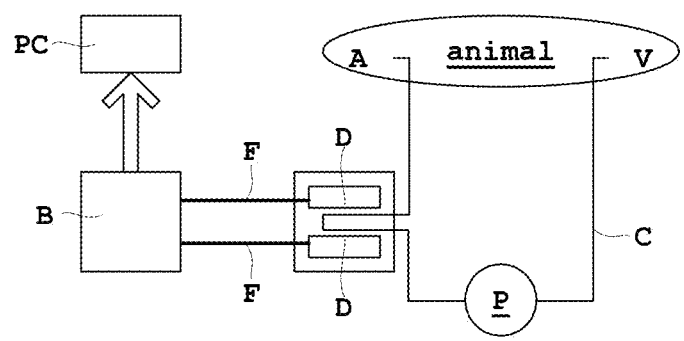
FIG. 7 schematically illustrates a blood collecting apparatus taking a conventional mode of pushing blood back to vein from one end of a catheter inserted into arteria.

(4) Moreover, as illustrated in FIG. 6, the target liquid to be collected (hatching with diagonal lines extending to the upper right) is sucked while a single flow path (tube) with no bifurcation is inserted into the container 11, and is pushed and pulled with the liquid L with which the flow path adjacent to the suction drain mechanism 5 is filled during a standby time as well as the suction drain mechanism 5, whereby the gas G is pushed and pulled. Consequently, movement of the target liquid to be collected is controlled. Such is adoptable. In FIG. 6, when the target liquid to be collected is drained and dropped, the flow path is removed from the container 11 and the liquid is drained from a dropping port of the flow path to a collecting container (not shown in FIG. 6). Accordingly, the flow path for sucking the liquid is shared with the flow path for dropping. In addition, the target liquid to be collected may be stopped immediately before the position of the supply source. Consequently, the construction illustrated in FIG. 6 does not always need the opening and closing device such as the pinch valve 7. Also in this modification, only the liquid L or the gas G may be the medium (fluid) to be pushed and pulled.

(5) In each of the present embodiments, the flow path is a tube. Alternatively, the flow path may be a groove on a substrate. In this case, the opening and closing device for opening and closing the flow path preferably opens and closes the groove using a valve, other than a pinch valve, that passes liquid inside.

(6) In the present embodiments, the opening and closing device for opening and closing the flow path is a pinch valve. Alternatively, as is described in the modification (5), the opening and closing device may be a valve, other than a pinch valve, that passing liquid inside.

(7) In the present embodiments, only a part of the flow path pinched with the pinch valve is a SILASCON tube, and the other part is formed by the first flow path and the second flow path. However, SILASCON is not limitative. For instance, each of the flow paths may be formed by a soft tube made of rubber having a restoring force, such as silicone, Tygon, and polyurethane. Alternatively, only the pinched part is not necessarily made of other materials. That is, the first flow path and the second flow path, or the first to third flow paths entirely may be made of the same material.

(8) In the embodiments mentioned above, the suction drain device (suction drain mechanism) repeatedly pushes and pulls the fluid with which the flow path is filled, whereby reciprocating movement of the target liquid to be collected is controlled. Alternatively, the fluid composed of the liquid and/or the gas may be pushed and pulled only in a period of time in the standby time in which coagulate may occur for controlling the movement of the target liquid to be collected.

Also in the modification, only the liquid L or the gas G may be the medium (fluid) to be pushed and pulled.

REFERENCE SIGN LIST

1 . . . blood collecting apparatus
2 . . . first flow path
3 . . . second flow path
4 . . . third flow path
5 . . . suction drain mechanism
$BL_1$ to $BL_3$ . . . blood
L . . . liquid
G . . . gas

The invention claimed is:

1. A liquid controlling method of controlling movement of a target blood to be collected in a blood collecting apparatus provided with a flow path having a given length, the flow path having a first end connected to a suction drain device for pushing and pulling blood and a second end, the method comprising steps of:
　filling a first portion of the flow path adjacent to the suction drain device with a fluid including a liquid and a gas with the second end of the flow path connected to an animal, wherein the fluid is not the target blood to be collected, and
　pushing and pulling the fluid adjacent to the suction drain device during a standby time between a collection of the target blood and a next collection of the target blood using the suction drain device with the second end of the flow path connected to the animal, whereby movement of the target blood to be collected is controlled,
　wherein the step of pushing and pulling the fluid adjacent to the suction drain device includes repeatedly reciprocating movement of the target blood to be collected such that coagulation of the target blood is prevented,
　wherein the blood fills a second portion of the flow path so that the gas is disposed between the blood and the liquid in the step of filling the first portion of the flow path with the fluid, and
　the second portion of the flow path is upstream of the first portion of the flow path.

2. The liquid controlling method according to claim 1, wherein the method comprises:
　filling the portion of the flow path adjacent to the suction drain device with the liquid,
　inserting the gas into the flow path between the liquid adjacent to the suction drain device and the target blood to be collected, and
　pushing and pulling the liquid adjacent to the suction drain device during the standby time using the suction drain device, causing the gas to be pushed and pulled.

3. The liquid controlling method according to claim 2, wherein the liquid with which the portion of the flow path adjacent to the suction drain device is filled is moved in the flow path, causing an inside of the flow path to be cleaned.

4. The liquid controlling method according to claim 2, wherein the gas has a volume in a range of 2 to 10 μL.

* * * * *